United States Patent [19]

Bigwood et al.

[11] Patent Number: 4,582,860

[45] Date of Patent: Apr. 15, 1986

[54] OXIRANE RESINS FOR ENZYME IMMOBILIZATION

[75] Inventors: Michael P. Bigwood, Oreland; John O. Naples, Dresher, both of Pa.

[73] Assignee: Rohm and Haas Company, Philadelphia, Pa.

[21] Appl. No.: 561,716

[22] Filed: Dec. 15, 1983

[51] Int. Cl.$^4$ .............................................. C08J 9/00
[52] U.S. Cl. ...................................... 521/56; 435/180; 521/60; 521/149
[58] Field of Search ........................... 521/149, 56, 60; 435/180

[56] References Cited

U.S. PATENT DOCUMENTS 4,070,348  1/1978  Kraemer et al. ................... 435/180
4,246,351  1/1981  Miyake et al. ...................... 521/149

Primary Examiner—Morton Foelak
Attorney, Agent, or Firm—J. E. Taylor, III

[57] ABSTRACT

Carriers for immobilizing enzymes may be prepared by suspension copolymerizing an oxirane-group-bearing, monovinyl monomer and a major amount of a trivinyl crosslinking monomer having a hydrophilic character, in the presence of a phase separator which does not react with the oxirane group. The resulting carriers, in bead form, have high porosity, high surface area, and pores of diameter sufficient for ready penetration by enzymes and substrates.

6 Claims, No Drawings

OXIRANE RESINS FOR ENZYME IMMOBILIZATION

This invention relates to immobilization of enzymes on oxirane-bearing polymer carriers. More particularly, it relates to an improved polymer bearing oxirane pendant groups, the polymer having high porosity, large-diameter pores, and high surface area.

BACKGROUND OF THE INVENTION

Enzymes are useful as catalysts in various reactions, and are preferably used in a purified form, separated from the organisms that produced them. In such a purified form the enzyme is relatively unstable and easily denatured, and it is also recovered with difficulty from an aqueous reaction medium. To overcome these difficulties, it is desirable to immobilize the enzyme on some insoluble carrier, where it may readily contact the reactants in the reaction medium, but where it benefits both from an increased stability and from easy recovery by simple processes such as filtration.

A conventional mechanism for immobilizing protein enzymes on a carrier is the reaction of an active hydrogen-bearing group, e.g., an alcohol, amine or mercaptan group, on the enzyme with an oxirane, or epoxy, ring pendant to an insoluble polymer, in which the ring is opened and the hydrogen from the enzyme group forms a hydroxyl group with the oxirane oxygen, as for example:

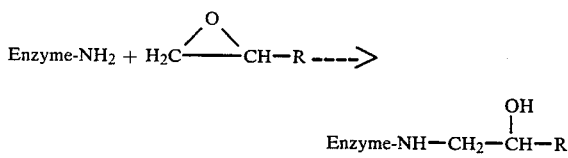

Thus, a carrier containing a significant fraction of oxirane rings may readily immobilize protein enzymes.

Such carriers have been prepared in the past in the form of beads with diameters from about 35 μm to about 2 mm, using conventional, suspension polymerization. Typical of such carriers are those described in U.S. Pat. Nos. 3,844,892 and 3,932,557. These references also teach many of the monomers containing the oxirane, or epoxy, ring.

The carriers described in the above references are conventional gel beads. As such, they have no permanent macroporosity and have a surface area approximately equal to that of spheres the same diameter as the beads. The enzymes tend to react at, and reside upon, the surface of these carriers, so increased surface area is highly desirable. Surface area of conventional, suspension-polymerized beads is typically increased by introducing macroporosity, usually by adding a phase separator, that is, a liquid which causes separation of the copolymer from the monomer phase. For such macroporosity to be useful in enzyme carriers, the pores must be large enough to permit the free passage of both the enzymes to be immobilized, and the components of the reaction medium. Methods for introducing macroporosity into the carrier beads have been reported, notably in British Pat. No. 1,512,462 and U.S. Pat. No. 4,070,348. These methods, however, produce carriers that have significant limitations for use in enzyme immobilization processes. The inverse suspension polymerization process of the U.S. reference, in which a water solution of monomers is suspended as droplets in an oil phase, produces carrier beads of relatively low surface area, while the alcohols employed as phase separators in the British reference react with the oxirane rings to reduce the number of available sites for enzyme immobilization.

THE INVENTION

We have discovered a carrier for enzyme immobilization which possesses both high surface area and a high density of active oxirane sites for enzyme immobilization, and a process for preparing this carrier. These carriers are macroporous beads prepared by free-radical suspension polymerization of glycidyl esters of acrylic or methacrylic acid, or allyl glycidyl ether, with a trivinyl monomer having a hydrophilic character, such as trimethylolpropane trimethacrylate, trimethylolpropane triacrylate, or triallyl isocyanurate, or mixtures thereof, in the presence of a phase separator which does not react with the oxirane ring. The ratio of monovinyl glycidyl compound to trivinyl compound may be from about 5:95 to about 95:5 by weight, with a preferred ratio from about 5:95 to about 50:50 by weight, and a more preferred ratio from about 10:90 to about 30:70 by weight. The preferred ratios promote the formation of carriers having a high surface area, with a correspondingly high level of oxirane groups available to immobilize enzymes.

The phase separator may be present in amounts ranging from about 20% to about 90% by weight, based on the weight of the organic phase. The phase separators which are suitable for the process of the present invention are those which do not react with the oxirane ring, but which still meet the generally accepted definition of phase separator given above. Examples of such phase separators include toluene, xylene, benzene, mesitylene, chloroform, ethylenedichloride, methyl isobutyl ketone, diisobutyl ketone, octane, and mixtures thereof. More preferred phase separators are hydrocarbon phase separators, and the most preferred phase extender is toluene.

A conventionl free-radical initiator, such as an azo or peroxide initiator, is used to initiate polymerization, in an amount from about 0.1 to about 4% by weight, based on the weight of the monomers. The organic phase, comprising the mixture of monomers and phase separator, is suspended with agitation in an aqueous suspension medium containing 1–10% by weight, based on the total weight of the suspension medium, of an inorganic salt that is not reactive with the monomers or initiator, preferably sodium choride, and 0.1 to 2% of conventional suspension aids, preferably gelatin and/or a sodium polyacrylate or polyvinyl alchol solution. The ratio of organic phase to aqueous phase is from about 0.5:1 to about 2:1.

The polymerization is carried out with agitation at a temperature high enough to cause decomposition of the initiator but low enough to prevent the organic or aqueous phases from boiling at the pressure selected, and preferably from about 40° C. to about 90° C. Atmospheric pressure is most commonly selected to avoid the use of pressure vessels, but pressures of several atmospheres may be employed if desired.

The resulting copolymer beads are macroporous and possess a high surface area. They also have pores large enough for ready penetration of enzymes or reactants, and they have a high density of oxirane groups that are available as sites for enzyme immobilization. These properties are demonstrated by the data in the examples below.

As enzymes are proteins, and all proteins have active hydrogen-bearing groups such as amines, alcohols or mercaptans which are available to react with the oxirane groups of the carrier, virtually all enzymes are suitable for immobilization on the carriers of the present invention. Some examples of enzymes which may be immobilized are penicillin G acylase, penicillin V acylase, glucoamylase, glucose isomerase, lactase, thermoase, cyanide hydrolase, cephalosporin hydrolase and esterase.

In addition to immobilization of enzymes, the oxirane rings of the carriers of the present invention are available to fix other materials bearing active hydrogens. Proteins other than enzymes may be immobilized by reactions identical to those of the enzyme proteins. Chiral groups such as amino acids may be bound, and this binding may be utilized to separate racemic mixtures of amino acids. Living cells may be immobilized to the carrier surfaces through reaction of their proteins. A particular application for which the carriers of the present invention are well suited is affinity chromatography, in which mixtures containing components which bind to the carriers are passed through a bed of the carriers. The components which bind are removed from the mixtures, and the remaining components pass unhindered through the bed. Similar uses will readily be apparent to those skilled in the art.

The following examples are intended to illustrate the invention, and not to limit it except as it is limited in the claims. All percentages are by weight except as otherwise noted, and all reagents indicated are of good commercial quality.

EXAMPLES

EXAMPLE 1

This example is intended to illustrate the preparation of an oxirine-bearing, porous polymer carrier, and immobilization of an enzyme thereupon.

An aqueous phase of 490 ml deionized water, 16.2 g sodium chloride, 10.5 g of a 12.5% solution of sodium polyacrylate (Acrysol ® GS dispersant) and 0.9 g Pharmagel TM gelatin dissolved in 50 ml deionized water was stirred in a reaction vessel for 10 minutes. An organic phase of 111.4 g trimethylolpropane trimethacrylate, 28.0 g glycidyl methacrylate, 314 g toluene and 1.35 g lauroyl peroxide was added to the vessel and the mixture was stirred at 200 RPM for 15 minutes. The temperature was then increased to 65° C. and maintained for 20 hours. The mixture was allowed to cool, and the resulting white beads were washed three times with 1000-ml portions of deionized water, followed by a single wash of 500 ml of toluene; the beads were then vacuum dried. A sample of the dried resin was rewet, and a 2-g portion was added to a mixture of 1 g freeze-dried penicillin acylase having an activity of 180 I.U./g and 4 ml of 1 M, pH-6 acetate buffer. The mixture was allowed to stand for 48 hours in the dark at room temperature; then the liquid phase was decanted, and the beads were placed in a chromatographic column. The beads were then washed by passing 250 ml aqueous, 1 M sodium chloride solution through the column, followed by 250 ml distilled water.

EXAMPLE 2

The process of Example 1 was repeated, except that 1.35 g azoisobuteronitrile was used in place of the lauroyl peroxide.

EXAMPLE 3

The process of Example 1 was repeated, except that the organic phase consisted of 124 g trimethylolpropane trimethacrylate, 14 g blycidyl methacrylate, 314 g toluene and 1.39 g lauroyl peroxide.

EXAMPLE 4

The process of Example 1 was repeated, except that the organic phase consisted of 99.2 g trimethylolpropane trimethacrylate, 42.2 g glycidyl methacrylate, 314.1 g toluene and 1.35 g lauroyl peroxide.

EXAMPLE 5

The process of Example 1 was repeated, except that after the third wash with 1000 ml of water, the residual toluene was removed by azeotropic distillation.

EXAMPLE 6

The procedure of Example 1 was repeated, except that the organic phase consisted of 71.0 g trimethylolpropane trimethacrylate, 71.0 g glycidyl methacrylate, 314.1 g toluene and 1.35 g lauroyl peroxide.

EXAMPLE 7

The procedure of Example 1 was repeated, except that the aqueous phase consisted of 1.1 g polyvinyl alcohol, 0.6 g Pharmagel TM gelatin and 617 g distilled water.

Table I, below, shows physical parameters of the carriers prepared in the above examples, and the activity of the penicillin acylase enzyme immobilized on the carriers. Surface area and porosity were determined from calculations based on the conventional Brunauer-Emmett-Teller (BET) nitrogen desorption isotherm test for surface area and mercury intrusion test for porosity. Surface oxirane activity was determined by the following procedure:

SURFACE OXIRANE ACTIVITY TEST

A 2-g sample of dry carrier resin was suspended wth stirring in 100 ml of 1.3 M aqueous sodium thiosulfate in a vessel connected to a pH controller, which electrometrically determined pH and metered in sufficient 0.1N hydrochloric acid to maintain the pH between 7.0 and 7.5. The amount of surface oxirane was calculated based on the reaction of sodium thiosulfate with the oxirane group to liberate an equivalent amount of sodium hydroxide.

The penicillin acylase activity of the carrier with immobilized enzyme, or of the free enzyme, was determined by the following procedure:

PENICILLIN ACYLASE ACTIVITY TEST

An amount of penicillin acylase enzyme, either free or immobilized on the carrier, sufficient to contain about 50 I.U. of activity, was suspended in 60 ml of 7.5-pH phosphate buffer. The mixture was maintained at 28° C. in a vessel connected to a pH controller which electrometrically determined the pH and metered in sufficient 0.8N sodium hydroxide solution to maintain the pH at approximately 8.0. A solution containing 5 g of penicillin G potassium salt in phosphate buffer, also at 28° C., was added to the vessel, and the rate of formation of phenylacetic acid by the enzyme-catalyzed hydrolysis of the penicillin G was determined from the rate of addition of sodium hydroxide solution to maintain the pH. The liquid in the vessel was sampled upon addition of the penicillin G salt and after 10 and 30 minutes. These samples (0.5 ml) were immediately mixed with 3 ml of a solution of 1 ml of 0.05M sodium hydroxide, 2 ml of 20% acetic acid and 0.5% (weight-volume) p-dimethylaminobenzaldehyde/methanol, and were allowed to stand for 10 minutes. The amount of 6-aminopenicillanic acid formed was determined by spectrophotometrically measuring the light absorption of the mixture at a wave length of 415 nm.

TABLE I

| Carrier of Example | Surface Area ($m^2/g$) | Porosity (cc/g) | Surface Oxiranes (meq/g) | Penicillin Acylase Activity (I.U./g wet) |
|---|---|---|---|---|
| 1 | 364 | 1.14 | 0.31 | 24 |
| 2 | 431 | 1.58 | 0.28 | 10.2 |
| 3 | 467 | 1.38 | 0.18 | 22.3 |
| 4 | 304 | 1.51 | 0.42 | 15.4 |
| 6 | 140 | 1.35 | 0.33 | 3.2 |

We claim:

1. A process for preparing an improved porous carrier bead for immobilized enzymes which process consists essentially of free-radical, suspension polymerizing an oxirane-group-bearing monovinyl monomer selected from the group consisting of glycidyl acrylate, glycidyl methacrylate, allyl glycidyl ether, and mixtures thereof, and a trivinyl crosslinking monomer having hydrophilic character, the ratio of monovinyl monomer to trivinyl monomer being from about 5:95 to about 50:50 by weight, in the presence of about 20% to about 90%, based on the weight of the organic phase, of a phase separator which does not react with the oxirane group, in an aqueous suspension medium.

2. The process of claim 1 wherein the ratio of monovinyl monomer to trivinyl monomer is from about 10:90 to about 30:70.

3. The process of claim 1 wherein the crosslinking monomer is selected from the group consisting of trimethylolpropane trimethacrylate, trimethylolpropane triacrylate, triallyl isocyanurate, or mixtures thereof.

4. The process of claim 1 wherein the phase separator is a hydrocarbon phase separator.

5. The process of claim 4 wherein the hydrocarbon phase separator is toluene.

6. The oxirane-group-bearing carrier for immobilized enzymes prepared by the process of claim 1.

* * * * *